United States Patent [19]

Bernhard et al.

[11] Patent Number: 5,670,548
[45] Date of Patent: Sep. 23, 1997

[54] PIGMENTATION WITH CAROTENOIDS

[75] Inventors: Kurt Bernhard, Lupsingen; Jiri Broz, Rheinfelden; Urs Hengartner, Basel; Paul Kreienbühl, Riehen; Katharina Schiedt, Arlesheim, all of Switzerland

[73] Assignee: Roche Vitamins Inc., Paramus, N.J.

[21] Appl. No.: 726,599

[22] Filed: Oct. 7, 1996

Related U.S. Application Data

[62] Division of Ser. No. 263,308, Jun. 21, 1994, Pat. No. 5,605,699.

[30] Foreign Application Priority Data

Jun. 24, 1993 [EP] European Pat. Off. ............. 93110074
Apr. 29, 1994 [EP] European Pat. Off. ............. 94106738

[51] Int. Cl.$^6$ ........................................ A01N 31/04
[52] U.S. Cl. ........................................ 514/725; 424/442
[58] Field of Search ........................ 514/725; 424/442

[56] References Cited

FOREIGN PATENT DOCUMENTS 4100739    7/1992    Germany.
93/122249  6/1993    WIPO.

OTHER PUBLICATIONS

English Language Abstract for DEX 4100739, 1992.
Isler, Carotenoids, pp. 12, 19–21, 669, 670 and 746–762 (1971).
Arpin et al., Phytochemistry 6:995–1005 (1967).
Britton et al., FEBS Letters 110:47–49 (1980).
Manchand et al., Tetrahedron Letters, 9: 989–991 (1966).
Barber et al., J. Chem. Soc. (C), pp. 2166–2176 (1966).
Schiedt et al., Pure and App. Chem., 63:89–100 (1991).
Vacherone and Michael, Phytochemistry, 8:897–903 (1969).
Takaichi et al., Arch. Microbiol., 155:473–476 (1991).
Hughes, Aust. J. Exp. Agric., 25:41–46 (1985).

*Primary Examiner*—D. Gabrielle Phelan
*Attorney, Agent, or Firm*—George W. Johnston; Dennis P. Tramaloni; Bruce A. Pokras

[57] ABSTRACT

A method of pigmenting certain parts and products of poultry, fish and crustacea by including in the feed of the pertinent animal one or more of the carotenoids 2'-dehydroplectaniaxanthin, desmethylspheroidenone, spheroidenone, 1-hydroxy-3,4-didehydro-1,2-dihydro-$\psi,\psi$-caroten-2-one, 5'-hydroxy-5',6'-dihydro-4'-apo-$\beta$-caroten-6'-one, 1'-hydroxy-3',4'-didehydro-1',2'-dihydro-$\beta,\psi$-carotene-4,2'-dione and 5'-hydroxy-5',6'-dihydro-4'-apo-$\beta$-carotene-4,6'-dione, poultry, fish and crustacea feeds for pigmenting certains parts and products of these animals, beadlets and premixes for adding to poultry, fish and crustacea feeds, and the carotenoids 1-hydroxy-3,4-didehydro-1,2-dihydro-$\psi,\psi$-caroten-2-one, 5'-hydroxy-5',6'-dihydro-4'-apo-$\beta$-caroten-6'-one, 1'-hydroxy-3',4'-didehydro-1',2'-dihydro-$\beta,\psi$-carotene-4,2'-dione and 5'-hydroxy-5',6'-dihydro-4'-apo-$\beta$-carotene-4,6'-dione.

5 Claims, No Drawings

PIGMENTATION WITH CAROTENOIDS

This is a division of application Ser. No. 08/263,308, filed Jun. 21, 1994, now U.S. Pat. No. 5,605,699.

BACKGROUND OF THE INVENTION

Carotenoids are natural pigments which occur abundantly in the plant and animal kingdoms and which in some cases have also been produced by synthetic means. Further synthetically produced carotenoids do not appear to occur in nature. Many important carotenoids are employed as pigments in the food and feedstuff industries, e.g. for colouring egg yolk, poultry, fish and crustaces, notably in the cases of ethyl β-apo-8'-carotenoate, citranaxanthin, canthaxanthin and astaxanthin. For this purpose the carotenoid pigments are added to the animals' rations as a method of imparting an enhanced and aesthetically more acceptable visual impression of colour, be it in the animal integuments, such as the skin, shanks and beaks of poultry and the skin, scales and shells of fish and crustaces, as appropriate, subcutaneous fat of poultry and the meat of fish and crustaces, or in such animal products as eggs (yolk). The enhancement of pigmentation depends on the particular light-absorbing conjugated double bond system of the carotenoid concerned, the degree of ease with which the carotenoid is taken up into the animal body following consumption of the carotenoid-enriched feed (deposition rate) and the concentration of the carotenoid or any metabolites in the target animal body tissue or product, amongst many other factors. However, from a knowledge of the structure of the selected carotenoid it cannot be predicted how effectively it functions as a pigment in this area of application. A further factor involved is the stability of the carotenoid, e.g. towards atmospheric oxidation, light, temperature and dampness, in an animal feedstuff when stored under the normal conditions to which such a feedstuff is subjected.

With respect to poultry an acceptable level and quality of pigmentation is desired for the integuments of the birds destined for consumption and for egg yolk. The use of materials to enhance yolk colour, for example, is generally promoted because consumers prefer deeply (particularly rich golden yellow) pigmented yolks. The visual appearance is indeed an important factor in the assessment of quality. Broilers and ornamental birds, for example, are in many parts of the world more aesthetically acceptable if their integuments, particularly skin, shanks and beaks, and in the case of broilers, also subcutaneous fat satisfy certain criteria of pigmentation. The need for supplementary pigmentation is especially prevalent today in view of the reduction of grass consumption with the modern methods of intensive poultry rearing, which involve the use of low fibre, high energy feeds, rendering difficult the production of well-pigmented poultry and egg yolks.

The pigmentation of fish meat and integuments, especially of various species of trout and salmon, and the meat and integuments of crustacea, especially of crabs, lobsters and shrimps, is also well known to be achieved by feeding the fish and crustacea with carotenoid-enriched feed preparations with a view to rendering the edible products more attractive to consumers.

It has now been found that certain carotenoids are surprisingly more effective as pigments in the above-indicated applications than the carotenoids known to have been used hitherto for such purposes. These carotenoids are 2'-dehydroplectaniaxanthin, desmethylspheroidenone, and spheroidenone (known), and 1-hydroxy-3,4-didehydro-1,2-dihydro-ψ,ψ-caroten-2-one, 5'-hydroxy-5',6'-dihydro-4'-apo-β-caroten-6'-one, 1'-hydroxy-3',4'-didehydro-1',2'-dihydro-β,ψ-carotene-4,2'-dione and 5'-hydroxy-5',6'-dihydro-4'-apo-β-carotene-4,6'-dione (novel). None of the known literature (including patent) references to the three known carotenoids indicate that these carotenoids can be used as pigments in the applications indicated hereinbefore, e.g. for enhancing the colour of egg yolk.

SUMMARY OF THE INVENTION

The present invention provides a method for pigmenting the egg yolk, integuments and subcutaneous fat of poultry and the meat and integuments of fish and crustacea by administering to the pertinent animal a feed composition which comprises one or more of the above three known carotenoids, 2'-dehydroplectaniaxanthin, desmethylspheroidenone, and spheroidenone, and/or one or more of the novel carotenoids 1-hydroxy-3,4-didehydro-1, 2-dihydro-ψ,ψ-caroten -2-one, 5'-hydroxy-5',6'-dihydro-4'-apo-β-caroten-6'-one, 1'-hydroxy-3',4'-didehydro-1',2'-dihydro-β,ψ-carotene-4,2'-dione and 5'-hydroxy-5',6'-dihydro-4'-apo-β-carotene-4,6'-dione. By pigmenting is meant adding pigment to the pertinent animal part or product in addition to the pigment that already occurs therein to produce a desired pigment, which may, for example, constitute a change of color, or an enhanced color. Any of the carotenoids of this invention may be used individually or in combination with any of the other carotenoids, to add pigment to the animal parts or products when fed to the pertinent animal in a feed composition.

Administration of the carotenoids may be accomplished by feeding the feed composition to the pertinent animal. Accordingly, also part of the invention is a feed composition-for poultry, fish or crustacea effective for pigmenting egg yolk, integuments and subcutaneous fat of poultry and the meat and integuments of fish and crustacea which comprises a poultry, fish or crustacea feed, as appropriate, and one or more of the above three known carotenoids and/or one or more of the above four new carotenoids.

In particular, the present invention provides a method of pigmenting the egg yolk, integuments and/or subcutaneous fat of poultry, and the meat and/or integuments of fish and crustacea by including one or more carotenoids in the feed of such poultry, fish or crustacea, characterized in that said carotenoids are 2'-dehydroplectaniaxanthin, desmethylspheroidenone, spheroidenone, 1-hydroxy-3,4-didehydro-1,2-dihydro-ψ,ψ-caroten-2-one, 5'-hydroxy-5',6'-dihydro- 4'-apo-β-caroten-6'-one, 1'-hydroxy-3',4'-didehydro-1',2'-dihydro-β,ψ-carotene-4,2'-dione and 5'-hydroxy-5',6'-dihydro-4'-apo-β-carotene -4,6'-dione.

The various aspects of the present invention preferably involve the use of 2'-dehydroplectaniaxanthin, followed in preference by desmethylspheroidenone or spheroidenone. Furthermore, these aspects are preferably applicable to the pigmenting of egg yolk of laying hens.

The present invention also provides a carotenoid-enriched feed for poultry, fish or erustacea and intended for the pigmentation of egg yolk, integuments and/or subcutaneous fat of the poultry and the meat and/or integuments of the fish and crustacea, characterized in that it contains as the carotenoid(s) one or more of 2'-dehydropleetaniaxanthin, desmethylspheroidenone, spheroidenone, 1-hydroxy-3,4- didehydro-1,2-dihydro-ψ,ψ-caroten-2-one, 5'-hydroxy-5',6'-dihydro-4'-apo-β-caroten-6'-one, 1'-hydroxy-3',4'-didehydro-1',2'-dihydro-β,ψ-carotene-4,2'-dione and 5'-hydroxy-5',6'-dihydro-4'-apo-β-carotene-4,6'-dione in an effective amount to pigment the above animal parts or products.

In this invention, poultry includes chickens, laying hens and broilers. Fish includes such fish as trout and salmon. Crustacea includes edible crustaceans such as lobster, crab and shrimp. Also, the term integuments includes in particular the skin, shanks and beaks of poultry and the skin, scales and shells of fish and crustacea.

DETAILED DESCRIPTION OF THE INVENTION

The carotenoids usable in the method and the carotenoid-enriched feed of the present invention are, in the case of the first, second and third mentioned carotenoids, known per se and indeed naturally occurring. The remaining four carotenoids are new compounds. The seven carotenoids have the following structural formulae. Relevant literature concerning the occurrence and/or chemical synthesis of the three known ones is given in parenthesis after the respective formulae.

2'-Dehydroplectaniaxanthin

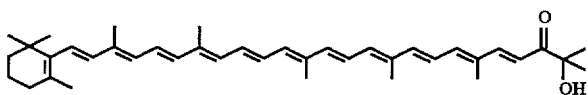

[Arpin et al., Phytochem. 6, 995–1005 (1967)]
Desmethylspheroidenone

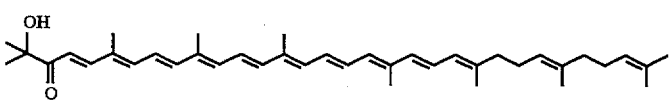

[Britton et al., FEBS Lett. 110, 47 (1980)]
Spheroidenone

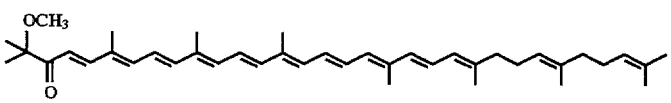

[Manchand et al., Tetr. Lett. 1966, 989; Barber et al., J. Chem. Soc. C 1966, 2166]

The four new carotenoids are:
1-Hydroxy-3,4-didehydro-1,2-dihydro-ψ,ψ-caroten-2-one

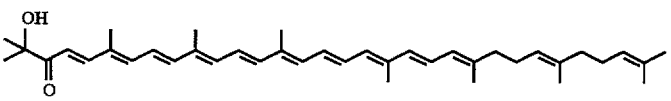

5'-Hydroxy-5',6'-dihydro-4'-apo-β-caroten-6'-one

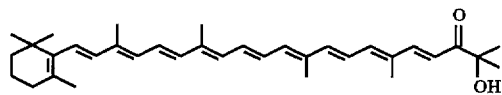

1'-Hydroxy-3',4'-didehydro-1',2'-dihydro-β,ψ-carotene-4,2'-dione

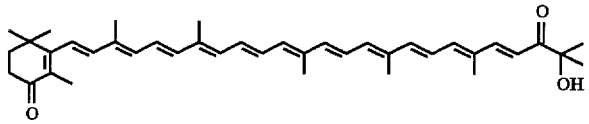

5'-Hydroxy-5',6'-dihydro-4'-apo-β-carotene-4,6'-dione

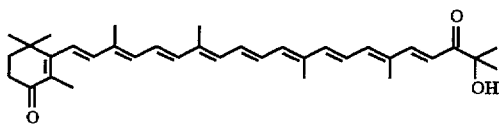

It will be noted from the foregoing formulae that all the carotenoids, with the exception of spheroidenone, feature a terminal 2-hydroxy-2-methyl-propionyl group [—COC(CH$_3$)$_2$OH]. Spheroidenone features the corresponding methylated group, viz. 2-methoxy-2-methyl-propionyl [—COC(CH$_3$)$_2$OCH$_3$] as the terminal group.

The four new carotenoids of this invention can be produced from appropriate starting materials by methods analogous to those for producing carotenoids of similar structure. Thus, the first of these, 1-hydroxy-3,4-didehydro-1,2-dihydro-ψ,ψ-caroten-2-one, can be produced by a method analogous to that for producing desmethyispheroidenone, viz. by condensing 4'-apo-ψ-caroten-4'-al with 3-hydroxy-3-methyl-2-butanone. In the case of 5'-hydroxy-5',6'-dihydro-4'-apo-β-caroten-6'-one, 1'-hydroxy-3',4'-didehydro-1',2'-dihydro-β,ψ-carotene-4,2'-dione and 5'-hydroxy-5',6'-dihydro-4'-apo-β-carotene-4,6'-dione the appropriate aldehyde, viz. 8'-apo-β-carotenal, 4-oxo-4'-apo-β-caroten-4'-al and 4-oxo-8'-apo-β-caroten-8'-al, respectively, is condensed in each case with the 3-hydroxy-3-methyl-2-butanone.

Each aldehyde may be obtained by known methods. For example, it may be produced conventionally by the known method of a base-catalyzed Wittig reaction of the appropriate lower aldehyde with the acetal of (3,7-dimethyl-8-oxo-2,4,6-octatrienyl)triphenylphosphonium chloride and subsequent acid catalyzed cleavage of the acetal group in the product of said Wittig reaction. This is illustrated for 4'-apo-ψ-caroten-4'-al in Example 5 hereinafter.

In general, each of the condensation reactions of the aldehyde with 3-hydroxy-3-methyl-2-butanone is suitably carried out in a conventional polar solvent, such as a lower alkanol, in particular methanol, ethanol, n-propanol, isopropanol or a butanol. The ketone reactant, 3-hydroxy-3-methyl-2-butanone, can itself also serve simultaneously as the solvent in this reaction. Furthermore, the reaction is effected in general at temperatures in the range from about 0° C. to about 100° C., preferably from room temperature to the reflux temperature of the reaction. mixture, and preferably in the presence of a base, such as sodium hydroxide, potassium hydroxide, an alkali metal alcoholate, e.g. sodium ethanolate, or triethylamine. hydroxide. The exclusion of air, conveniently by conducting the reaction under an atmosphere of inert gas, e.g. argon, is recommended. If the product is a cis/trans (Z/E) mixture, the desired (all-E) product may be formed by heating the mixture in a lower alkane, preferably n-heptane. This is a conventional procedure for such a carotenoid isomerization.

Part of this invention is a method for pigmenting egg yolk, integuments and subcutaneous fat of poultry and the meat and integuments of fish and crustacea comprising administering to the pertinent animal, specifically by feeding, a carotenoid-enriched feed composition. The composition contains poultry, fish or crustacea feed, as appropriate, and one or more of the following carotenoids: 2'-dehydroplectaniaxanthin, desmethylspheroidenone, spheroidenone, 1-hydroxy-3,4-didehydro-1,2-dihydro-ψ,ψ-caroten-2-one, 5'-hydroxy-5',6'-dihydro-4'-apo-β-caroten-6'-one, 1'-hydroxy-3',4'-didehydro-1',2'-dihydro-β,ψ-carotene-4,2'-dione and 5'-hydroxy-5',6'-dihydro-4'-apo-β-carotene-4,6'-dione. The amount of the carotenoid or carotenoids added is effective to produce pigmented parts or products of the animal which has been fed the composition. This pigmentation is determined by analyzing the pigment of a resulting animal part or product and can be done visually, and the amount of carotenoid in the part or product can also be determined. For example, a change in pigment may be determined by visual comparison with the animal part or product to which carotenoids of this invention have not been added. These analyses can be performed by conventional methods such as any optical analysis and, for example, as described in Example 1. Of the carotenoids so used the most preferred one is 2'-dehydroplectaniaxanthin. Also preferred are desmethylspheroidenone and spheroidenone. Any amount of carotenoids described above, either individually or in any combination, may be used in this method in an amount effective to pigment the animal parts or products.

In particular, a feed composition in which the total carotenoid content is 0.1 milligram of carotenoid or carotenoids per kilogram of feed (mg/kg) to 150 mg/kg of feed, is generally suitable in the method. This method can be specifically applied to poultry, such as chickens, laying hens and broilers, providing pigment to poultry parts or products such as egg yolk, subcutaneous fat, or integuments (including skin, shanks, and beaks). A feed composition which has a carotenoid(s)/feed content of 0.25 mg/kg to 20 mg/kg is preferred, especially for pigmenting poultry parts or products. This method is especially useful for pigmenting the yolks of eggs of laying hens, and pigmenting broilers. This method is also useful for pigmenting fish or crustacea, in particular their meat and integuments (skin, scales and shells, as appropriate). In this case the composition preferably contains 2.5 mg to 150 mg carotenoid or carotenoids per kg.

For realizing the method of the present invention the carotenoid is applied by known methods via any conventional poultry, fish or crustacea feed, as appropriate, and in these circumstances the carotenoid responsible for the enhanced pigmentation is ingested by the pertinent animal in a natural manner. The feed may also contain other carotenoids which themselves contribute to the normal pigmentation of egg yolk, integuments and/or subcutaneous fat of poultry and the meat and/or integuments of fish and crustacea. However, to obtain the added pigmentation of this invention, one or more of the seven carotenoids whose names and structural formulae are given hereinabove is added. The content of added carotenoid(s) in the feed is generally in the range 0.1 ppm to 150 ppm (mg/kg or 0.00001 to 0.015% by weight) based on the total weight of the carotenoid-enriched feed. In poultry feed, in particular for laying hens and broilers, the content of added carotenoid (s) is preferably in the range 0.25 ppm to 20 ppm, and in the case of feed for fish or crustacea this content is preferably in the range 2.5 ppm to 150 ppm.

Also part of this invention is a feed composition for poultry, fish or crustacea and effective for pigmenting egg yolk, integuments and subcutaneous fat of poultry and the meat and integuments of fish and crustacea in respect of the animal to which it has been fed comprising a poultry, fish or crustacea feed, as appropriate, and one more of the following carotenoids: 2'-dehydroplectaniaxanthin, desmethylspheroidenone, spheroidenone, 1-hydroxy-3,4-didehydro-1,2-dihydro-ψ,ψ-caroten-2-one, 5'-hydroxy-5',6'-dihydro-4'-apo-β-caroten-6'-one, 1'-hydroxy-3',4'-didehydro-1',2'-dihydro-β,ψ-carotene-4,2'-dione and 5'-hydroxy-5',6'-dihydro-4'-apo-β-carotene-4,6'-dione, i.e., the carotenoids of this invention. The amount of the carotenoid or carotenoids is effective to add pigment to the parts or products of the animal to which the composition has been fed. As stated above, effective pigmentation can be determined by conventional methods such as visual inspection of the animal product, and the amount of carotenoid or carotenoids present in the part or product can also be quantified. The determination can also be effected by any conventional means of optical analysis and as described in Example 1. The feed compositions described above may also contain only the carotenoid or carotenoids 2'-dehydroplectaniaxanthin, desmethylspheroidenone and spheroidenone. Alternatively, the feed composition may contain only one or more of the new carotenoids indicated above. A most preferred carotenoid is 2'-dehydroplectaniaxanthin, also preferred are desmethylspheroidenone and spheroidenone.

A further feed composition of this invention comprises a poultry, fish or crustacea feed and one or more of the following carotenoids: 2'-dehydroplectaniaxanthin, desmethylspheroidenone, spheroidenone, 1-hydroxy-3,4-didehydro-1,2-dihydro-ψ,ψ-caroten-2-one, 5'-hydroxy-5',6'-dihydro-4'-apo-β-caroten-6'-one, 1'-hydroxy-3',4'-didehydro-1',2'-dihydro-β,ψ-carotene-4,2'-dione and 5'-hydroxy-5',6'-dihydro-4'-apo-β-carotene-4,6'-dione. The carotenoid content of this composition is 0.1 mg to 150 mg of carotenoid or carotenoids/kg of feed (or 0.00001 to 0.015% by weight). A poultry, fish or crustacean feed, in particular a poultry feed, is part of this invention. A feed composition having an amount of carotenoid or carotenoids of 0.25 to 20 mg/kg of feed (0.25 ppm to 20 ppm) is preferred, especially as a poultry feed. A feed composition having an amount of carotenoid or carotenoids of 2.5 mg/kg to 150 mg/kg (2.5 ppm to 150 ppm) is also preferred, especially as a fish or crustacean feed.

All the feed compositions of this invention when formulated as conventional feed for poultry are especially useful to pigment such animal products as yolks produced by laying hens, and also to pigment the subcutaneous fat and integuments of poultry. The feed compositions of this invention are also useful formulated as conventional fish or crustacean animal feeds, and pigment animal parts such as integuments and meat of these animals. Pigmentation is obtained by feeding the feed compositions of this invention to the animal in question.

The poultry, fish and crustacea feed compositions of this invention may be any conventional animal feeds formulated for the pertinent animal to be fed by conventional means, to which the one or more of the carotenoid or carotenoids 2'-dehydroplectaniaxanthin, desmethylspheroidenone, spheroidenone, 1-hydroxy-3,4-didehydro-1,2-dihydro-ψ,ψ-caroten-2-one, 5'-hydroxy-5',6'-dihydro-4'-apo-β-caroten-6'-one, 1'-hydroxy-3',4'-didehydro-1',2'-dihydro-β,ψ-carotene-4,2'-dione and 5'-hydroxy-5',6'-dihydro-4'-apo-β-carotene-4,6'-dione are added. The ingredients of the feed composition according to the present invention are well known, and the feed can also be produced by conventional methods, involving physical admixture, pelleting, extrusion, microencapsulation, spraying etc., whereby at some stage during the production process one or more of the seven carotenoids is/are incorporated.

The conventional ingredients of poultry feed include, for example. wheat, maize, barley, sorghum, oats, rice and/or soybean meal, usually in ground or broken form, as appropriate, in major proportions (at least about 10 percent by weight in each case). Further ingredients in minor amounts (up to about 5 percent by weight, or in certain cases less than 1 percent by weight) include, for example, fish, meat and/or bone meal, wheat bran, straw, yeast, hydrolysed fat, tallow, lard, limestone, salt, methionine premix, mineral premix, vitamin premix and/or anticaking agent. Any poultry feed can be enriched with one or more of the seven carotenoids to afford a poultry feed according to the present invention. Typical fish or crustacea feeds of the present invention include, apart from the added carotenoid(s), fish meal, as the major source of proteins, wheat and bone meal, soybean meal, wheat flour, cooked starch, yeast, fish oil, soybean oil, soya lecithin, methionine, vitamins and minerals. The protein, lipids and carbohydrate contents of such a feed are approximately 40–50%, 15–30% and 10% by weight, respectively.

The carotenoids or carotenoid mixtures of the invention for incorporation in the poultry, fish or crustacea feed can be mixed in the form of beadlets into a so-called premix, which in turn is added to the feed. The beadlets themselves, which represent a further aspect of the present invention, conveniently contain, apart from the carotenoid(s), any suitable matrix such as a starch-coated matrix of gelatin and carbohydrate, and one or more suitable anti-oxidants, e.g. ethoxyquin and/or ascorbyl palmitate.

Thus, this invention also includes such a beadlet or a premix, either of which may be added to any conventional poultry, fish or crustacea feed composition to provide a feed composition effective for pigmenting parts or products of the pertinent animal to which it is fed. When the premix or beadlet is added to the feed, the amount of carotenoid or carotenoids in the premix or beadlet is effective to cause the added pigmentation of this invention when the poultry, fish or crustacea are fed the feed composition to which the beadlet or premix has been added. Pigmentation is determined by conventional means as described above. The beadlet or premix each contains one or more of the following carotenoids: 2'-dehydroplectaniaxanthin, desmethylspheroidenone, spheroidenone, 1-hydroxy-3,4-didehydro-1,2-dihydro-ψ, ψ-caroten-2-one, 5'-hydroxy-5', 6'-dihydro-4'-apo-β-caroten-6'-one, 1'-hydroxy-3',4'-didehydro-1',2'-dihydro-β,ψ-carotene-4,2'-dione and 5'-hydroxy-5',6'-dihydro-4'-apo-β-carotene-4,6'-dione in an amount effective to pigment animal products when added to an animal feed composition. The carotenoids used may in particular be one or more of the novel carotenoids, as indicated hereinbefore, or one or more of 2'-dehydroplectaniaxanthin, desmethylspheroidenone or spheroidenone. A most preferred carotenoid is 2'-dehydroplectaniaxanthin. Also preferred are desmethylspheroidenone and spheroidenone.

The feed compositions may specifically be conventionally formulated for poultry or fish or crustacea, as described. A preferred animal product for pigmentation is a poultry egg yolk, for example obtained by feeding a composition as described to a laying hen. The beadlets of this invention are. conventionally formulated and may comprise a suitable conventional coating matrix and antioxidant in addition to carotenoid(s). A suitable matrix is for example gelatin and carbohydrate. Anti-oxidants may be ethoxyquin or ascorbyl palmitate. The beadlets may be coated with a conventional coating substance such as starch. A preferred carotenoid content of a beadlet is 1% to 20% carotenoid or carotenoids by weight of beadlet.

The premix is made of a conventional carrier material which is ultimately present in the animal feed composition as described, in particular such a composition for poultry, fish or crustacea, and a carotenoid or carotenoids described above. A preferred carotenoid content of the premix is 0.001% to 15% by weight of premix of carotenoid or carotenoids.

The beadlets generally contain from 1 to 20 percent by weight of one or more of 2'-dehydroplectaniaxanthin, 1-hydroxy-3,4-didehydro-1,2-dihydro-ψ,ψ-caroten-2-one, desmethylspheroidenone, spheroidenone, 5'-hydroxy-5',6'-dihydro-4'-apo-β-caroten-6'-one, 1'-hydroxy-3',4'-didehydro-1,2'-dihydro-β,ψ-carotene-4,2'-dione and 5'-hydroxy-5',6'-dihydro-4'-apo-β-carotene-4,6'-dione as the active ingredient, whereas the premix generally contains from 0.001 to 15% by weight of the active ingredient.

The invention is illustrated by the following Examples, which are intended to illustrate but not limit the invention.

EXAMPLE 1

Four carotenoids never previously reported to have been used for pigmenting egg yolk, namely 2'-dehydroplectaniaxanthin, 1-hydroxy-3,4-didehydro-1,2-dihydro-ψ,ψ-caroten-2-one, desmethylspheroidenone and spheroidenone (in this and the following Examples hereinafter referred to as carotenoid A, B, C and D, respectively) were evaluated for their egg yolk pigmenting efficacy in a primary green with laying hens, and compared with the known pigmenting carotenoid canthaxanthin (the "positive control") under the same conditions.

Each of the four carotenoids was formulated as beadlets of the following composition:

Carotenoid-containing beadlet composition:

| Constituent | Percent by weight |
|---|---|
| Carotenoid A/B/C/D | 7.0/3.5/6.0/6.0 |
| Ethoxyquin | 1.0 |
| Ascorbyl palmitate | 1.0 |
| Gelatin, Bloom No. 140 | 38.5 |
| Dextrin yellow | 15.7 |
| Crystalline sugar | 15.7 |
| Fluidized corn starch approx. | 21.1/24.6/22.1/22.1 |
| Total | 100.0 |

Then the beadlets of each carotenoid A–D and of canthaxanthin were incorporated into low-carotenoid basal diets to such an extent that the content (inclusion level) of the test carotenoid was in each case 10 mg/kg diet. The basal diet supplemented with carotenoid A, carotenoid B or canthaxanthin contained in addition 0.70–1.40 ppm of lutein and 0.20–0.50 ppm of zeaxanthin, and the basal diet supplemented with carotenoid C, carotenoid D or canthaxanthin contained in addition 0.85–1.20 ppm of lutein and 0.20–0.35 ppm of zeaxanthin, as well as in each case a normal level of supplemental vitamins. The compositions of the low-carotenoid basal diets are presented in the following Tables 1 and 2:

TABLE 1

Composition of low carotenoid basal diet used for carotenoids A and B

| Ingredients | Content in weight percent |
|---|---|
| Wheat, ground | 37.00 |
| Oats, ground | 11.00 |
| Rice, broken | 13.00 |
| Soybean meal | 10.00 |
| Fish meal [70% crude protein (CP)] | 5.00 |
| Meat meal, full fat (82% CP) | 1.30 |
| Wheat bran | 3.50 |
| Straw (NaOH treated) | 2.40 |
| Yeast | 1.00 |
| Hydrolysed fat | 3.60 |
| Ground limestone | 9.55 |
| Salt | 0.20 |
| Methionine premix (25%) | 0.50 |
| Anticaking agent (Diamol ®) | 1.00 |
| Mineral premix (trace elements) | 0.20 |
| Vimmin premix * | 0.75 |
| Calculated content (weight percent): | |
| Crude protein (%) | 16.80 |
| Metabolizable energy (MJ/kg) | 11.39 |
| Crude fibre (%) | 3.78 |
| Crude fat (%) | 5.77 |
| Calcium (%) | 4.22 |
| Phosphorus (%) | 0.43 |

*consisting of, per kg feed:
Vitamin A 8000 IU, vitamin $D_3$ 1800 IU, vitamin E 60 mg, vitamin $K_3$ 1.3 mg, vitamin C 200 mg, vitamin $B_1$ 4 mg, vitamin $B_2$ 11.8 mg, vitamin $B_6$ 8 mg, vitamin $B_{12}$ 0.04 mg, biotin 0.06 mg, Ca-pantothenate 48 mg, nicotinic acid 104 mg, folic acid 2 mg, choline 1950 mg.

TABLE 2

Composition of low carotenoid basal diet used for carotenoids C and D

| Ingredient | Content in weight percent |
|---|---|
| Wheat, ground | 35.00 |
| Sorghum, ground | 20.00 |
| Oats, ground | 11.00 |
| Soybean meal | 10.00 |
| Fish meal (64% CP) | 3.00 |
| Meat med (60% CP) | 4.00 |
| Wheat bran | 5.60 |
| Yeast | 1.00 |
| Hydrolyzed fat (50% free fatty acids) | 1.80 |
| Ground limestone | 7.00 |
| Salt | 0.19 |
| Methionine premix (25%) | 0.50 |
| Mineral premix (trace elements) | 0.20 |
| Vitamin premix * | 0.71 |
| Calculated content (weight percent): | |
| Crude protein (%) | 17.29 |
| Metabolizable energy (MJ/kg) | 11.43 |
| Crude fibre (%) | 3.49 |
| Crude fat (%) | 4.57 |
| Calcium (%) | 3.26 |
| Phosphorus (%) | 0.56 |

*see Table 1

The incorporated carotenoids A–D and canthaxanthin were checked for content in the feed by HPLC.

The laying hens used in the test were kept in individual cages in a 3-floor battery. In the case of the carotenoids A and B and the canthaxanthin used for comparison 72 Isa Brown hens of age 42 weeks were involved, whereby six replicate groups, each of three hens, were assigned to each dietary treatment with one of the three carotenoids, and without (negative control, i.e. basal diet without added test carotenoid). The situation was analogous for the carotenoids C and D and the pertinent canthaxanthin, whereby however four replicate groups each consisting of six Lehmann LSL hens of age 61 weeks were involved, drawing on a total of 96 hens.

Before the actual trial the hens were fed the above-indicated low carotenoid basal diet in order to reduce the existing egg yolk pigmentation. Then, during the 3 weeks trial, the hens were fed the same low carotenoid basal diets supplemented with the test carotenoid or containing no such carotenoid (negative control). The feed, in mash form, and water were provided "ad libitum". The laying performance of the hens was monitored once weekly, and the last two eggs per hen were collected for the laboratory assays.

The pigmenting efficacy was assessed by means of colour description, accompanied with photographic documentation and reflectance colour measurements (CIE Yxy system), as well as by measurement of carotenoid deposition in the egg yolk. The reflectance measurements were effected using the Gardner XL colorimeter, and the determined tristimulus values were converted into the CIE system of values of dominant wavelength and spectral saturation [see J. P. Vuilleumier, The "Roche Yolk Colour Fan"—An Instrument for Measuring Yolk Colour, Poultry Science 48, 767–779 (1969)] The dominant wavelength and spectral saturation values from the reflectance measurements were subjected to analysis of variance, using the ANOVA program (SAS, 1985). To evaluate the differences among treatment means Duncan's multiple range test was utilized (alpha=0.05). The carotenoid deposition measurements, which gave the levels of the test carotenoids in pooled egg yolks, were determined by the same HPLC methods as used for the determination of the carotenoid levels in the diets before feeding, and involved the quantification of the carotenoid originally incorporated in the feed.

The results (average values) are presented in the following tables, viz. Tables 3 and 4:

TABLE 3

Egg yolk pigmenting efficacy of carotenoids

| Carotenoid | Dominant wavelength (nm) | Spectral saturation | Level of carotenoid in egg yolk (ppm) |
|---|---|---|---|
| A | 626.7 | 0.649 | 24.1 |
| B | 612.7 | 0.496 | 5.3 |
| Canthaxanthin | 592.3 | 0.855 | 30.6 |
| none (negative control) | 578.1 | 0.465 | — |

TABLE 4

Egg yolk pigmenting efficacy of carotenoids

| Carotenoid | Dominant wavelength (nm) | Spectral saturation | Level of carotenoid in egg yolk (ppm) |
|---|---|---|---|
| C | 599.5 | 0.777 | 20.75 |
| D | 596.3 | 0.782 | 17.23 |
| Canthaxanthin | 589.9 | 0.853 | 25.25 |
| none (negative control) | 575.8 | 0.477 | — |

The results show that all four carotenoids and canthaxanthin markedly affected the pigmentation of egg yolks. Carotenoid A (2'-dehydroplectaniaxanthin) resulted in an extremely carmine red pigmentation of egg yolks, which was reflected in the enhancement of the dominant wavelength from 578.1 to 626.7 nm. Although the spectral saturation was moderate, a remarkably high level (24.1 ppm) was found in egg yolk. Carotenoid B (1-hydroxy-3,4-didehydro-1,2-dihydro-$\psi$, $\psi$-caroten-2-one) markedly enhanced the dominant wavelength to 612.7 nm, although this effect was associated with a limited deposition and colour saturation, resulting in a pale pink pigmentation of egg yolks. Both carotenoid C (desmethylspheroidenone) and carotenoid D (spheroidenone) showed good potency, producing red pigmentation of egg yolk and markedly increasing the dominant wavelengths (from 575.8 to 599.5 nm and to 596.3 nm, respectively) and spectral saturation (from 0.477 to 0.777 and to 0.782, respectively). They were also readily deposited in egg yolks (20.75 and 17.23 ppm). Canthaxanthin used as the positive control in this case showed a red-orange pigmentation of egg yolks. The dominant wavelength was markedly lower than for carotenoids C and D (589.9 nm), the spectral saturation higher (0.853) and the deposition in egg yolks also higher (25.25 ppm).

EXAMPLE 2

Using an analogous procedure to that described in Example 1 desmethylspheroidenone (hereinafter "carotenoid C") and canthaxanthin, as the positive control, were each evaluated at graded levels of 1, 2 and 4 ppm in combination with a basal level of 4 ppm of ethyl β-apo-8'-carotenoate ("apo-ester") for their egg yolk pigmenting efficacy in a primary screen with laying hens. In each case the individual carotenoid was formulated as beadlets before being incorporated into the low carotenoid basal diets to the above-indicated extents. Such beadlets contained 6.1 weight percent of desmethylspheroidenone, or 10.4 weight percent of canthaxanthin, or 11.3 weight percent of apo-ester, as appropriate, whereby these weight percents were confirmed by spectrophotometric data. The composition of the low-carotenoid basal diets, which contained 0.70–1.40 ppm of lutein and 0.20–0.50 ppm of zeaxanthin as well as normal levels of supplemental vitamins, is presented in the following Table 5:

TABLE 5

Composition of low carotenoid basal diet used for carotenoid combinations carotenoid C + apo-ester and canthaxanthin + apo-ester

| Ingredients | Content in weight percent |
|---|---|
| Wheat, ground | 35.00 |
| Oats, ground | 11.00 |
| Rice, broken | 20.00 |
| Soybean meal | 10.00 |
| Fish meal (70% CP) | 3.00 |
| Meat and bone meal (40% CP) | 4.00 |
| Wheat bran | 5.50 |
| Yeast | 1.00 |
| Hydrolysed fat | 1.85 |
| Ground limestone | 7.00 |
| Salt | 0.20 |
| Methionine premix (25%) | 0.50 |
| Mineral premix (trace elements) | 0.20 |
| Vitamin premix* | 0.75 |
| Calculated content (weight percent): | 16.70 |
| | 11.25 |
| Crude protein (%) | 3.15 |
| Metabolizable energy (MJ/kg) | 4.07 |
| Crude fibre (%) | 3.67 |
| Crude fat (%) | 0.69 |
| Phosphorus (%) | |

*see Table 1

The incorporated carotenoids were checked for content in the feed by HPLC.

The laying hens used in the tests were kept in individual cages in a 3-floor battery. 72 Isa Brown hens of age 40 weeks were involved, whereby four replicate groups of three hens were assigned to each dietary treatment with a particular carotenoid combination as above.

Before the actual trial the hens were fed the above-indicated low carotenoid basal diet in order to reduce the existing egg yolk pigmentation. Then, during the 3 weeks trial, the hens were fed the same low carotenoid basal diets supplemented with the test carotenoid combinations. The feed, in mash form, and water were provided "ad libitum". The laying performance of the hens was monitored once weekly, and the last two eggs per hen were collected for the laboratory assays.

As in Example 1, the pigmenting efficacy was assessed by means of colour description, accompanied with photographic documentation and reflectance colour measurements, as well as by means of carotenoid deposition in the egg yolk. In respect of the reflectance colour measurements, the egg yolk colour was determined by using either the traditional CIE colour triangle (Yxy system) or the modern CIELAB system. Furthermore, the colour of pooled yolks from each replicate group was scored by means of the Roche Yolk Colour Fan 1989 (RYCF). For further details see Example 1.

The results (average values) are presented in the following tables, viz. Tables 6 and 7:

TABLE 6

Egg yolk pigmenting efficacy of carotenoid combinations (visual scoring dominant wavelength, spectral saturation and level in egg yolk)

| Carotenoid C/Canthaxanthin + Apo-ester (inclusion level in ppm) | Visual scoring RYCF* value | Dominant wavelength (nm) | Spectral saturation | Level in egg yolk (ppm) | Carotenoid |
|---|---|---|---|---|---|
| Carotenoid C (1) + Apo-ester (4) | 12.0 | 585.14 | 0.848 | 2.6 | 17.1 |
| Carotenoid C (2) + Apo-ester (4) | 15.0 | 588.43 | 0.843 | 4.9 | 16.0 |
| Carotenoid C (4) + Apo-ester (4) | 15.0 | 592.55 | 0.842 | 10.3 | 15.4 |
| Canthaxanthin (1) + Apo-ester (4) | 10.0 | 582.01 | 0.859 | 2.6 | 16.8 |
| Canthaxanthin (2) + Apo-ester (4) | 11.0 | 583.21 | 0.856 | 4.4 | 15.2 |
| Canthaxanthin (4) + Apo-ester (4) | 12.3 | 585.81 | 0.876 | 10.9 | 17.5 |

*RYCF = Roche Yolk Colour Fan

TABLE 7

Egg yolk pigmenting efficacy of carotenoid combinations (yolk colour measurements with the CIELAB system)

| Carotenoid C/ Canthaxanthin + Apo-ester (Inclusion level in ppm) | Lightness L* | Redness a* | Yellowness b* | Hue h*ab | Chroma C*ab |
|---|---|---|---|---|---|
| Carotenoid C (1) + Apo-ester (4) | 56.63 | 14.94 | 47.45 | 72.52 | 49.75 |
| Carotenoid C (2) + Apo-ester (4) | 53.25 | 20.20 | 42.69 | 64.66 | 47.23 |
| Carotenoid C (4) + Apo-ester (4) | 49.69 | 25.50 | 37.71 | 55.92 | 45.54 |
| Canthaxanthin (1) + Apo-ester (4) | 59.09 | 9.42 | 51.41 | 79.62 | 52.26 |
| Canthaxanthin (2) + Apo-ester (4) | 58.65 | 12.56 | 50.79 | 76.11 | 52.33 |
| Canthaxanthin (4) + Apo-ester (4) | 56.15 | 18.88 | 49.31 | 69.05 | 52.81 |

The results show that carotenoid C (desmethylspheroidenone) was deposited to a similar extent as canthaxanthin in egg yolks but revealed a considerably higher potency than canthaxanthin in respect of the egg yolk pigmenting efficacy. The pigmentation achieved with the combination of carotenoid C and apo-ester was a very desirable yellow-orange.

EXAMPLE 3

Using an analogous procedure to that described in Example 1, 2'-dehydroplectaniaxanthin (hereinafter "carotenoid A") and canthaxanthin, citranaxanthin and ethyl 4'-apo-β-caroten-4'-oate (neurosporaxanthin ethyl ester), as three positive controls, were each evaluated at graded levels of 0.5, 1 and 2 ppm (carotenoid A) or 1, 2 and 4 ppm (each of the three positive controls), in combination with a basal level of 4 ppm of ethyl-β-apo-8'-carotenoate ("apo-ester") for their egg yolk pigmenting efficacy in a primary screen with laying hens. In each case the individual carotenoid was formulated as beadlets before being incorporated into the low carotenoid basal diets to the above-indicated extents. Such beadlets contained 6.5 weight percent of 2'-dehydroplectaniaxanthin, or 10.0 weight percent of canthaxanthin, or 11.1 weight percent of citranaxanthin, or 6.4 weight percent of neurosporaxanthin ethyl ester, or 10.4 weight percent of apo-ester, as appropriate, whereby these weight percents were confirmed by spectrophotometric data. The composition of the low-carotenoid basal diets, which contained 0.70–1.40 ppm of lutein and 0.20–0.50 ppm of zeaxanthin as well as normal levels of supplemental vitamins, is presented in the following Table 8:

TABLE 8

Composition of low carotenoid basal diet used for the carotenoid combinations carotenoid A + apo-ester, canthaxanthin + apo-ester, citranaxanthin + apo-ester and neurosporanxanthin ethyl ester + apo-ester

| Ingredients | Content in weight percent |
|---|---|
| Wheat, ground | 37.00 |
| Oats, ground | 11.00 |
| Rice, broken | 13.00 |
| Soybean meal | 10.00 |
| Fish meal (70% CP) | 5.00 |
| Meat meal, full fat (82% CP) | 1.30 |
| Wheat bran | 3.50 |
| Straw (NaOH treated) | 2.40 |
| Yeast | 1.00 |
| Hydrolysed fat | 3.60 |
| Ground limestone | 9.55 |
| Salt | 0.20 |
| Methionine premix (25%) | 0.50 |
| Anticaking agent (Diamol ®) | 1.00 |
| Mineral Premix (trace elements) | 0.20 |
| Vitamin premix* | 0.75 |
| Calculated content (weight percent): | |
| Crude protein (%) | 16.80 |
| Metabolizable energy (MJ/kg) | 11.39 |
| Crude fibre (%) | 3.78 |
| Crude fat (%) | 5.77 |
| Calcium (%) | 4.22 |
| Phosphorus (%) | 0.43 |

*see Table 1

The incorporated carotenoids were checked for content in the feed by HPLC.

The laying hens used in the tests were kept in individual cages in a 3-floor battery. 144 Isa Brown hens of age 72 weeks were involved, whereby four replicate groups of three hens were assigned to each dietary treatment with a particular carotenoid combination as above.

Before the actual trial the hens were fed the above-indicated low carotenoid basal diet in order to reduce the existing egg yolk pigmentation. Then, during the 3 weeks trial, the hens were fed the same low carotenoid basal diets supplemented with the test carotenoid combinations. The feed, in mash form, and water were provided "ad libitum". The laying performance of the hens was monitored once weekly, and the last two eggs per hen were collected for the laboratory assays.

As in Example 1, the pigmenting efficacy was assessed by means of colour description, accompanied with photographic documentation and reflectance colour measurements, as well as by means of carotenoid deposition in the egg yolk. In respect of the reflectance colour measurements, the egg yolk colour was determined by using either the traditional CIE colour triangle (Yxy system) or the modern CIELAB system. Furthermore, the colour of pooled yolks from each replicate group was scored by means of the Roche Yolk Colour Fan 1989 (RYCF). For further details see Example 1.

The results (average values) are presented in the following tables, viz. Tables 9 and 10:

TABLE 9

Egg yolk pigmenting efficacy of carotenoid combinations (visual scoring dominant wavelength, spectral saturation and level in egg yolk

| Carotenoid A/ Canthaxanthin/ Citranaxathin/ Neurosporaxanthin ethyl ester + Apo-ester (inclusion level in ppm) | Visual scoring RYCF* value | Dominant wavelength (nm) | Spectral saturation | Level of carotenoid in egg yolk (ppm) | |
|---|---|---|---|---|---|
| | | | | Carotenoid A/Canthax-anthin/Citran-axathin/Neurospor-axanthin ethyl ester | Apo-ester |
| Carotenoid A (0.5) + Apo-ester (4) | 13.0 | 587.1 | 0.849 | 1.5 | 18.4 |
| Carotenoid A (1) + Apo-ester (4) | 14.0 | 589.8 | 0.840 | 3.0 | 18.4 |
| Carotenoid (2) + Apo-ester (4) | >15.0 | 595.0 | 0.831 | 6.6 | 19.1 |
| Canthaxanthin (1) + Apo-ester (4) | 10.0 | 583.7 | 0.865 | 3.3 | 18.8 |
| Canthaxanthin (2) + Apo-ester (4) | 12.0 | 585.7 | 0.876 | 6.9 | 19.7 |
| Canthaxanthin (4) + Apo-ester (4) | 13.0 | 587.5 | 0.882 | 12.5 | 17.8 |
| Citranaxanthin (1) + Apo-ester (4) | 10.0 | 583.1 | 0.862 | 1.7 | 18.0 |
| Citranaxanthin (2) + Apo-ester (4) | 11.0 | 583.8 | 0.869 | 2.5 | 18.8 |
| Citranaxanthin (4) + Apo-ester (4) | 12.0 | 585.4 | 0.868 | 5.0 | 17.7 |
| Neurosporaxanthin ethyl ester (1) + Apo-ester (4) | 12.0 | 584.4 | 0.864 | 2.9 | 17.2 |
| Neurosporaxanthin ethyl ester (2) + Apo-ester (4) | 13.0 | 587.1 | 0.871 | 5.3 | 17.6 |
| Neurosporaxanthin ethyl ester (4) + Apo-ester (4) | 14.0 | 590.2 | 0.874 | 9.6 | 17.0 |

*RYCF = Roche Yolk Colour Fan

TABLE 10

Egg yolk pigmenting efficacy of carotenoid combinations (yolk colour measurements with the CIELAB system)

| Carotenoid A/ Canthaxanthin/ Citranaxanthin/ Neurospora-xanthin ethyl ester + Apo-ester (Inclusion level in ppm) | Light-ness L* | Redness a* | Yellowness b* | Hue h*ab | Chroma C*ab |
|---|---|---|---|---|---|
| Carotenoid A (0.5) + Apo-ester (4) | 55.31 | 15.07 | 45.76 | 71.77 | 48.18 |
| Carotenoid A (1) + Apo-ester (4) | 52.59 | 20.34 | 40.87 | 63.51 | 45.65 |
| Carotenoid A (2) + Apo-ester (4) | 48.40 | 26.21 | 31.74 | 50.44 | 41.17 |
| Canthaxanthin (1) + Apo-ester (4) | 59.19 | 10.62 | 52.37 | 78.53 | 53.44 |

TABLE 10-continued

Egg yolk pigmenting efficacy of carotenoid combinations (yolk colour measurements with the CIELAB system)

| Carotenoid A/<br>Canthaxanthin/<br>Citranaxanthin/<br>Neurospora-<br>xanthin ethyl ester +<br>Apo-ester<br>(Inclusion level in ppm) | Light-<br>ness<br>L* | Redness<br>a* | Yellowness<br>b* | Hue<br>h*ab | Chroma<br>C*ab |
|---|---|---|---|---|---|
| Canthaxanthin (2) + Apo-ester (4) | 57.65 | 15.18 | 51.41 | 73.58 | 53.62 |
| Canthaxanthin (4) + Apo-ester (4) | 55.75 | 19.43 | 49.07 | 68.39 | 52.78 |
| Citranaxanthin (1) + Apo-ester (4) | 59.27 | 8.97 | 51.82 | 80.18 | 52.60 |
| Citranaxanthin (2) + Apo-ester (4) | 58.90 | 11.02 | 51.94 | 78.03 | 53.09 |
| Citranaxanthin (4) + Apo-ester (4) | 56.91 | 15.44 | 50.60 | 73.05 | 52.92 |
| Neurosporaxanthin ethyl ester (1) + Apo-ester (4) | 57.50 | 14.29 | 50.17 | 74.11 | 52.17 |
| Neurosporaxanthin ethyl ester (2) + Apo-ester (4) | 55.56 | 19.24 | 47.93 | 68.15 | 51.65 |
| Neurosporaxanthin ethyl ester (4) + Apo-ester (4) | 53.80 | 24.08 | 45.89 | 62.31 | 51.82 |

The results presented in Tables 9 and 10 clearly show that carotenoid A (2'-dehydroplectaniaxanthin) is a far more potent red carotenoid for egg yolk pigmentation than canthaxanthin, citranaxanthin or neurosporaxanthin ethyl ester. Taking the dominant wavelength as a parameter, its efficacy in the tests at 0.5 and 1 ppm was, for example, approximately 4 times higher than that of neurosporaxanthin ethyl ester and almost 7 times higher than that of canthaxanthin.

EXAMPLE 4

Preparation of 5'-Hydroxy-5',6'-dihydro-4'-apo-β-caroten-6'-one

A solution of 12.5 g (30 mmol) of 8'-apo-β-carotenal in 200 ml of methanol is introduced at room temperature under an atmosphere of argon into a 750 ml 4-necked reaction flask fitted with a 4.5 cm Teflon® stirring blade, a thermometer and an intensive cooler. To the solution are then added 20 ml (95% pure, 180 mmol) of 3-hydroxy-3-methyl-2-butanone, and thereafter, with stirring and within 30 minutes, a solution of 2 g (50 mmol) of sodium hydroxide in 40 ml of water, the addition being conducted dropwise. To the resulting suspension are added a further 100 ml of methanol, and the whole is then warmed at 40° C. using an oil bath. A dark-coloured solution results. After approximately 48 hours the reaction is established by thin layer chromatography to be virtually complete. The resulting solution is neutralized with 3.15 ml (50 mmol) of glacial acetic acid and is allowed to cool slowly to room temperature, whereby dark coloured crystals are precipitated. To promote the precipitation the solution is cooled further in an ice bath. After 2 hours the whole is filtered, and the collected precipitate washed with 100 ml of cold methanol.

The precipitate is crystallized from a mixture of methylene chloride and hexane, affording the desired 5'-hydroxy-5',6'-dihydro-4'-apo-β-caroten-6'-one as almost black crystals. These are filtered off, washed with hexane and dried at 40° C. under a reduced pressure of 20 mbar. The yield of product is 13.57 g (83% of the theoretical yield). M.p. 179°–180° C.

EXAMPLE 5

Preparation of (all-E)-1-hydroxy-3,4-didehydro-1,2-dihydro-ψ,ψ-caroten-2-one 1.80 g (17 mmol) of trimethyl orthoformate and 0.4 ml of a 1% (w/v) solution of p-toluenesulphonic acid in methanol are added to a solution of 6.34 g (14.2 mmol) of (3,7-dimethyl-8-oxo-2,4,6-octatrienyl)triphenylphosphonium chloride in 30 ml of methanol. The mixture is stirred at room temperature under argon for 1½ hours and then quenched with 0.2 ml of pyridine. The dimethylacetal of (3,7-dimethyl-8-oxo-2,4,6-octatrienyl)triphenylphosphonium chloride is thereby produced. A solution of 4.31 g (12.3 mmol) of (all-E)-12'-apo-ψ-caroten-12'-al [prepared according to the method of Hengartner et al., Helv. Chim. Acta 75, 1848 (1992)] in 50 ml of methylene chloride is then added to the mixture, which is cooled to –20° C. A freshly prepared solution of sodium methoxide, prepared by dissolving 363 mg (15.8 mmol) of sodium metal in 5 ml methanol, is added at –20° C. over 30 minutes and the mixture is stirred at room temperature for 2 hours and then acidified with 0.8 ml of concentrated sulphuric acid in 10 ml of ice-water. The mixture is stirred for 20 minutes and then mixed with 50 ml of methylene chloride and 60 ml of ice-water. The organic phase is washed with aqueous sodium bicarbonate solution and brine, dried and concentrated. The residue is taken up in 80 ml of methylene chloride. Then the methylene chloride is distilled off on a rotary evaporator while 320 ml of methanol is simultaneously added. After stirring the solution at 0° C. for 1 hour the resulting dark red crystals are collected by filtration and dried, affording 4.85 g (82% of the theoretical yield) of (all-E)-4'-apo-ψ-caroten-4'-al, m.p. 166°–167° C.

8.94 g (87 mmol) of 3-hydroxy-3-methyl-2-butanone are added to a solution of 1.54 g (23 mmol) of potassium hydroxide (86%) in 14 ml of methanol under argon. Then a solution of 4.22 g (8.7 mmol) of the (all-E)-4'-apo-ψ-caroten-4'-al in 50 ml of methylene chloride is added at 10° C. over 30 minutes. The mixture is stirred at room temperature for 64 hours and then neutralized with 1.6 ml of acetic acid. The methylene chloride is distilled off on a rotary evaporator while 70 ml of methanol are simultaneously added. The resulting suspension is filtered and the filter cake washed with methanol and dried. Recrystallization from methylene chloride/methanol (solvent exchange) affords 4.10 g (83% of the theoretical yield) of (all-E)-1-hydroxy-3,4-didehydro-1,2-dihydro-ψ,ψ-caroten-2-one as dark violet crystals, m.p. 199° C.

EXAMPLE 6

Preparation of (all-E)-1'-hydroxy-3',4'-didehydro-1',2'-dihydro-β,ψ-carotene -4,2'-dione A mixture of 2.82 g (5.68 mmol) of 4-oxo-4'-apo-β-caroten-4'-al, 1.22 ml/1.159 g (11.37 mmol) of 3-hydroxy-3-methyl-2-butanone and 0.063 ml of 9-molar aqueous potassium hydroxide solution (5.68 mmol KOH) in 20 ml of propanol is heated by means of an oil bath to 73°–75° C. After about 2 hours at this temperature the reaction is established by thin layer chromatography to be complete.

The cooled mixture is extracted with a two-phase solvent system of methylene chloride and ice water containing a little 1N sulphuric acid until the aqueous phase is neutral.

After separation of the two phases the organic phase is dried over anhydrous sodium sulphate and subsequently concentrated by, evaporation under reduced pressure. The resulting dark red oil is chromatographed through silica gel using a 2:1 mixture of diethyl ether and hexane as the eluant. Combination of the fractions containing the carotenoid product and evaporation under reduced pressure affords a dark red residue. which is then submitted to isomerization by heating a solution of said residue in heptane at 100° C. for about 16 hours. Thereafter the solution is cooled to 0° C. and the resulting dark red crystals (1.50 g; 46% of the theoretical yield) are filtered off. The product, 1'-hydroxy-3',4'-didehydro-1',2'-dihydro-β,ψ-carotene- 4,2'-dione, has a melting point of 181°–182° C. and an (all-E) content of 92% according to HPLC; UV/VIS (hexane+1% $CH_2Cl_2$+1% $C_2H_5OH$): 501 nm (ε=154,000).

EXAMPLE 7

Preparation of (all-E-)-5'-hydroxy-5',6'-dihydro-4'-apo-β-carotene-4,6'-dione

To a suspension of 2.15 g (5 mmol) of 4-oxo-8'-apo-β-caroten-8'-al in 20 ml propanol is added a solution of 1.02 g (10 mmol) of 3-hydroxy-3-methyl-2-butanone in 0.55 ml of 9-molar aqueous potassium hydroxide (5 mmol KOH), and the mixture is heated to 72°–74° C. in an oil bath. The initially heterogeneous mixture becomes homogeneous within 20 minutes heating time, and within about 45 minutes crystallization begins to occur.

The mixture is then cooled to about 0°–5° C. and filtered, and the crystals are washed in turn with methanol, water (to neutrality of the filtrate), methanol and hexane and dried at 30° C. under reduced pressure. In this way there are obtained 1.94 g (75% of the theoretical yield) of (all-E)-5'-hydroxy-5',6'-dihydro-4'-apo-β-carotene-4,6'-dione, m.pt. 189°–191° C. and of approx. 99% purity according to HPLC.

We claim:

1. Carotenoids 1-hydroxy-3,4-didehydro-1,2-dihydro-ψ,ψ-caroten-2-one, 5'-hydroxy-5',6'-dihydro-4'-apo-β-caroten-6'-one, 1'-hydroxy-3',4'-didehydro-1',2'-dihydro-β,ψ-carotene-4,2'-dione and 5'-hydroxy-5',6'-dihydro-4'-apo-β-carotene-4,6'-dione.

2. A carotenoid of claim 1 which is 1-hydroxy-3,4-didehydro-1,2-dihydro-ψ,ψ-caroten-2-one.

3. A carotenoid of claim 1 which is 5'-hydroxy-5',6'-dihydro-4'-apo-β-caroten-6'-one.

4. A carotenoid of claim 1 which is 1'-hydroxy-3',4'-didehydro-1',2'-dihydro-β,ψ-carotene-4,2'-dione.

5. A carotenoid of claim 1 which is 5'-hydroxy-5',6'-dihydro-4'-apo-β-carotene-4',6'-dione.

* * * * *